(12) United States Patent
Peuker et al.

(10) Patent No.: US 9,486,298 B2
(45) Date of Patent: Nov. 8, 2016

(54) CARTRIDGE FOR DISPENSING A DENTAL SUBSTANCE AND METHOD OF ASSEMBLING THE CARTRIDGE

(75) Inventors: Marc Peuker, Schondorf (DE); Helmut Pauser, Diessen (DE); Jens Gramann, Gräfelfing (DE); Andreas J. Boehm, Reichling (DE); Manfred Harre, Landsberg am Lech (DE)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days.

(21) Appl. No.: 14/235,148

(22) PCT Filed: Jul. 27, 2012

(86) PCT No.: PCT/US2012/048567
§ 371 (c)(1),
(2), (4) Date: Jan. 29, 2014

(87) PCT Pub. No.: WO2013/016645
PCT Pub. Date: Jan. 31, 2013

(65) Prior Publication Data
US 2014/0158711 A1    Jun. 12, 2014

(30) Foreign Application Priority Data

Jul. 28, 2011   (EP) ..................................... 11175729

(51) Int. Cl.
*G01F 1/05*  (2006.01)
*A61C 5/06*  (2006.01)
*B05C 17/005*  (2006.01)
(Continued)

(52) U.S. Cl.
CPC .............. *A61C 5/068* (2013.01); *A61C 5/064* (2013.01); *B05C 17/00553* (2013.01); *B05C 17/0133* (2013.01); *B65B 1/04* (2013.01)

(58) Field of Classification Search
CPC  B65D 81/325; B65D 83/0011; A61C 5/068; A61C 5/064; B65B 1/04; B05C 17/0133; B05C 17/00553
USPC ...... 222/136, 325, 333, 145.1, 390; 401/175
See application file for complete search history.

(56) References Cited

U.S. PATENT DOCUMENTS

| | | | | |
|---|---|---|---|---|
| 2,625,302 | A | * | 1/1953 | Mahoney .......................... 222/82 |
| 3,774,816 | A | * | 11/1973 | Bratton .......................... 222/391 |
| 4,046,288 | A | | 9/1977 | Bergman |
| 4,240,566 | A | | 12/1980 | Bergman |

(Continued)

FOREIGN PATENT DOCUMENTS

| | | |
|---|---|---|
| DE | 19727340 | 2/1998 |
| DE | 29819661 | 2/1999 |

(Continued)

OTHER PUBLICATIONS

International Search Report for PCT/US2012/048567 mailed Sep. 5, 2012.

*Primary Examiner* — Kevin P Shaver
*Assistant Examiner* — Robert Nichols, II (57) ABSTRACT

Provided is a cartridge assembly comprising a cartridge for containing a dental substance. The cartridge comprises a dispensing opening for the dental substance. Further the cartridge assembly comprises a piston having a receptacle for establishing a screw connection with a spindle for moving the piston for dispensing the dental substance. This assembly helps minimize costs in the manufacturing and use of dental cartridges and/or dental dispensing devices.

14 Claims, 5 Drawing Sheets

(51) Int. Cl.
  *B05C 17/01* (2006.01)
  *B65B 1/04* (2006.01)

(56) References Cited

U.S. PATENT DOCUMENTS

| | | | | |
|---|---|---|---|---|
| 5,249,709 A | * | 10/1993 | Duckworth | B05C 17/00506 222/137 |
| 5,333,760 A | * | 8/1994 | Simmen | 222/137 |
| 6,022,163 A | * | 2/2000 | Asfur | A45D 24/22 132/112 |
| 6,071,028 A | * | 6/2000 | Klawson | 401/75 |
| 6,075,314 A | | 6/2000 | Huettinger | |
| 6,176,396 B1 | * | 1/2001 | Hamada et al. | 222/137 |
| 6,311,871 B1 | | 11/2001 | Binder | |
| 6,319,002 B1 | | 11/2001 | Pond | |
| 2008/0247805 A1 | * | 10/2008 | deVirag et al. | 401/139 |

FOREIGN PATENT DOCUMENTS

| | | |
|---|---|---|
| EP | 2324792 | 5/2011 |
| RU | 705266 | 12/1979 |
| WO | WO 2007126656 | 11/2007 |

\* cited by examiner

FIG. 8b

CARTRIDGE FOR DISPENSING A DENTAL SUBSTANCE AND METHOD OF ASSEMBLING THE CARTRIDGE

CROSS REFERENCE TO RELATED APPLICATIONS

This application is a national stage filing under 35 U.S.C. 371 of PCT/US2012/048567, filed 27 Jul. 2012, which claims priority to European Application No. 11175729.0 filed 28 Jul. 2011, the disclosure of which is incorporated by reference in its/their entirety herein.

FIELD

The invention relates to a cartridge assembly for use in dispensing a dental substance, and in particular to a cartridge assembly having a cartridge and a piston, with the piston being configured to engage with a spindle for driving the piston. The invention further relates to a method of assembling the cartridge assembly.

BACKGROUND

A variety of dental substances are provided in packages which do not only allow for storing the substances but further enable the substances to be dispensed directly from the package. In particular dental impression materials are often provided in cartridges or bags which can be used in a motor powered device to dispense and mix portions of material from those.

For example US-A-2007/0158362 discloses a dispensing cartridge, particularly for dental impression materials. The dispensing cartridge can be used in a motor driven device for dispensing and mixing the dental material.

Although there are certain packages for use with motor or manually driven dispensing devices there is still a need for a package which is easy to use and relatively inexpensive.

SUMMARY

In a first aspect the invention relates to a cartridge assembly, comprising a cartridge for containing a dental substance. The cartridge assembly is removably placeable in a dispensing device for dispensing a dental substance. The cartridge of the cartridge assembly comprises a dispensing opening for the dental substance. Further the cartridge assembly comprises a spindle, and a piston which has a receptacle for establishing a screw connection with a spindle for moving the piston. The movement of the piston enables urging the dental substance toward the dispensing opening. The cartridge assembly comprises a coupling for coupling the spindle and a drive of a dispensing device for driving the spindle.

The invention may be advantageous in minimizing time for preparation of a dental substance before use. Further the invention may allow for a relatively compact design of a dispensing device for use with the cartridge assembly. The invention may allow for minimizing a force or pressure a device has to provide for dispensing dental substance from the cartridge assembly. Thus the invention may allow for configuring a device for dispensing a dental substance at minimized pressure capacity. Accordingly a relatively light weight device may be achieved. Further a device operating at minimized power consumption may be achieved. The invention may further provide for a cartridge assembly which can be operated manually as well as by a motor driven device. Thus a user using the cartridge assembly manually may be easily upgraded with a dispensing device which can operate the same type of cartridge assembly automatically. The invention may also allow for relatively precise metering of dental substance. The invention further may provide for a device which is easy to use and relatively inexpensive.

In one embodiment the cartridge assembly has a longitudinal axis which may correspond to a center axis of the cartridge. The cartridge may have a circumferential cartridge side wall which extends along the longitudinal axis. For example the cartridge may have a cartridge side wall which has a generally cylindrical inner surface with the cylinder axis co-aligned with the longitudinal axis. The cartridge side wall may further have a generally cylindrical outer surface which is concentric with the cylindrical inner surface of the cartridge side wall. The cartridge may further have a front end with a cartridge front wall through which the dispensing opening may extend. Further the cartridge may be open at a rear end and therefore may have a rear opening. The cartridge preferably forms a chamber for receiving the dental substance. Such chamber is preferably formed by the inner surface of the cartridge side wall and an inner surface of the cartridge front wall. The chamber therefore may open into the dispensing opening and in the rear opening of the cartridge. The piston may be received in the cartridge through the rear opening. In particular the piston is preferably arranged within the chamber of the cartridge. The piston and the cartridge are preferably retained against rotation relative to each other only by friction. The piston is preferably arranged within the cartridge for a movement along the longitudinal axis. Further the cartridge assembly is preferably adapted such that the spindle can be received within the cartridge, in particular within the chamber of the cartridge. The spindle extends along a spindle axis, which may be a rotation axis of the spindle. The cartridge assembly is preferably adapted for arrangement of the spindle with the spindle axis parallel to the longitudinal axis of the cartridge, in particular with the spindle generally co-aligned with the longitudinal axis. Preferably the dispensing opening has a smaller cross-sectional area than the cylindrical inner surface of the cartridge. Thus a movement of the piston by a first length preferably causes a strand of dental substance having a greater second length to be dispensed. Such a greater length may be measured relatively easy. Therefore the cartridge assembly may allow for relatively precise metering of the dental substance.

In one embodiment the cartridge of the cartridge assembly has a support at the front end. The support may allow for positioning the cartridge in a device for dispensing the dental substance, for example in a motorized device. The support may be formed by a generally convex or conical shape of the front end of the cartridge.

In one embodiment the cartridge assembly comprises the spindle. The spindle may however be replaceable in the cartridge assembly, and/or reusable for a plurality of cartridge assemblies. This may for example help minimizing costs for making the cartridge assembly.

In one embodiment the receptacle comprises a through-hole through the piston. For example the piston may have a generally cylindrical shape. The cylinder axis of the piston corresponds to a piston axis which is preferably co-aligned to the longitudinal axis. The piston may be formed of at least a piston front wall and a peripheral outer piston wall. The through-hole preferably extends through the piston front wall in a dimension parallel to the piston axis. The through-hole may extend generally concentrically about the piston axis. However in one embodiment the through-hole may extend in an off-center relationship to piston axis. Accordingly the screw connection between the receptacle and the spindle may be established with the spindle and the piston arranged concentrically, or in one embodiment with the spindle and the piston arranged in an off-center relationship. The off-center arrangement may cause the piston and the spindle to rotate relative to each other and prevent the piston and the cartridge to rotate relative to each other in case the spindle and the cartridge are twisted relative to each other. In one embodiment the cartridge assembly may also comprise two generally parallel spindles. The spindles and the piston may be adapted such that the spindles rotated in opposite directions cause the piston to move the piston for dispensing the dental substance. Due to the rotation in opposite directions the torques applied to the spindles for rotating the spindles may compensate. Thus a rotation of the spindles may substantially not cause the piston and the cartridge to rotate relative to each other.

In one embodiment the piston has a peripheral outer piston seal. The outer piston seal is preferably adapted for providing a seal between the cartridge and the piston. For example the outer piston seal may prevent the dental substance from flowing through a gap between the cartridge and the piston. The outer piston seal may be part of the outer piston wall, or attached to it. For example the outer piston seal may be a lip seal protruding from the outer piston. The outer piston seal may extend generally conically with the cone widening (or having the greater cone diameter) toward the dispensing opening. Thus a pressure built up in the cartridge for dispensing the dental substance preferably also urges an end of the lip seal toward the cartridge. Therefore the lip seal is preferably adapted such that the sealing force between the piston and the cartridge increases with the force the piston is advanced for dispensing material increasing. The skilled person will recognize alternative seal structures which likewise provide for an increasing seal effect with the pressure the seal is exposed to increasing.

In one embodiment the receptacle has a thread for engaging with a thread of the spindle. The skilled person will recognize that instead of one of the threads another engagement member may be used. For example the spindle may have a thread and the receptacle may have a pin or partial thread for engaging the thread of the spindle. Further the receptacle may have a thread and the spindles may have a plurality of pins or partial threads for engaging the thread of the receptacle.

In one embodiment the receptacle is deformable and adapted for forming an engagement with a spindle thread by deformation through the spindle. For example the receptacle may have a through-hole having a smaller inner diameter than the outer diameter of the spindle thread. In another example the receptacle may have a through-hole with a smaller inner diameter than the minor diameter of the spindle thread. The spindle may be turned into the receptacle and thereby a ridge of the thread may squeeze into the wall forming the through-hole. Thus a thread may be formed in the receptacle by turning the spindle into the receptacle. This may provide a generally play-free screw connection. Further the screw connection may as such form a seal between the piston and the spindle, for example so that an additional seal may not be needed.

In one embodiment the receptacle and the spindle are press fit for providing a seal between the receptacle and the spindle. In this embodiment both, the receptacle in the piston and the spindle may have threads which are sized and shaped to form a press fit in combination. A screw connection having a piston and a spindle of this embodiment may as such form a seal between the piston and the spindle.

In one embodiment the receptacle comprises an inner cone and the spindle comprises an outer cone. The cartridge assembly may be adapted such that the inner and outer cone in one position of the piston and the spindle relative to each other are in touch to seal the receptacle, whereas in another position of the piston and the spindle relative to each other the cones are spaced. Thus a relatively tight seal during storage of the cartridge assembly may be achieved.

In one embodiment the piston has an inner piston seal. The inner piston seal is preferably adapted for providing a seal between the piston and the spindle. For example the inner piston seal may prevent the dental substance from flowing through a gap between the piston and the spindle. The inner piston seal may be part of the piston, or attached to it. For example the inner piston seal may be a lip seal protruding from a wall forming the through-hole or from the piston front wall. The inner piston seal may extend generally conically with the cone narrowing (or having the smaller cone diameter) toward the dispensing opening. Thus a pressure built up in the cartridge for dispensing the dental substance preferably also urges an end of the lip seal toward the spindle. Therefore the lip seal is preferably adapted such that the sealing force between the piston and the spindle increases with the force the piston is advanced for dispensing material increasing.

In a further embodiment the receptacle comprises or forms a clasp nut. For example the piston may be formed of two parts or portions each comprising a groove, and in combination of the two parts or portions the grooves may form one common through-hole through the piston. The walls forming the grooves or through-hole may be threaded as described above, and thus a threaded clasp nut may be formed. This may facilitate assembly of the piston and spindle relative to each other.

In one embodiment the cartridge assembly comprises a support wheel for supporting the spindle in the cartridge. The support wheel may carry the spindle, for example may form one piece with the spindle. Preferably the support wheel and the spindle are coaxially arranged with each other. The support wheel may be received in the rear opening of the cartridge. Therefore the support wheel may center the spindle within the chamber of the cartridge.

In a further embodiment the piston and the cartridge are rotationally retained relative to each other, and the piston and the spindle are rotatable relative to each other. Further the spindle and the cartridge may be axially retained relative to each other, and the piston and the cartridge may be axially displaceable relative to each other. The term "axially" in this regard preferably relates to a rotation axis of the plunger and cartridge relative to each other or a rotation axis of the piston and the spindle relative to each other. Thus a rotation of the spindle preferably causes the piston to displace axially, and accordingly to urge the dental substance toward the dispensing opening. This may be further advantageous in that a majority of the force required for dispensing the dental substance may be picked up by the cartridge assembly itself and may not need to be provided from outside to the cartridge assembly. For example a relatively small force for rotating the cartridge and the spindle relative to each other may be sufficient to urge the dental substance forward at a higher force. Therefore the cartridge assembly may allow for providing a motorized dispensing device which runs at minimized power consumption and minimized forces.

In one embodiment the cartridge assembly has a first operation interface allowing for manual operation of the cartridge assembly, for example for manual dispensation of the dental substance from the cartridge assembly. The cartridge assembly has a second operation interface allowing for machine operation of the cartridge assembly, for example for dispensation of the dental substance by a motorized dispensing device.

The second operation interface is a coupling of the cartridge assembly. Thus the cartridge assembly comprises a coupling for coupling the spindle and a drive of a dispensing device for driving the spindle. The coupling may comprise a gear structure. Further the coupling may comprise a non-circular engagement structure. Such engagement structure may be any male or female structure allowing for engagement with a corresponding counter-structure of a drive of a dispensing device. Example of non-circular engagement structures comprise, but are not limited to, a pin or hole extending at a polygonal cross-sectional shape, like a triangle, square, hexagon, or any other suitable shape.

In one embodiment the cartridge assembly has a closure for openably closing the dispensing opening. Such closure and the cartridge may be movable relative to each other between an open position, in which the dispensing opening is open, and a closed position, in which the dispensing opening is closed. Thus the closure and the cartridge may in combination form a slide valve for the dispensing opening, for example a rotary slide valve.

In a further embodiment the cartridge assembly comprises a cutter for cutting off a portion of the dental substance which protrudes over the dispensing opening. For example the cutter may be formed by the closure. The closure may have an orifice which is at least partially formed by a cutting edge forming the cutter. In the open position the orifice may at least partially overlap the dispensing opening. Upon a movement toward the closed position the cutting edge may cut or shear off dental substance which protrudes over the dispensing opening, and in the closed position a wall of the cartridge may cover the dispensing opening.

In one embodiment the dispensing opening and the orifice have generally circular cross-sections. Other shapes of the opening and the orifice are however possible. Further the dispensing opening and the orifice may have different sizes and/or shapes. Preferably the dispensing opening has a smaller diameter or cross-sectional area than the orifice. Thus the surface forming the orifice may not be contaminated with dental substance during dispensation.

In one embodiment the closure forms a cap which is adapted for receiving the front end of the cartridge. The cap and the cartridge may be retained relative to each other against separation but may be rotatable relative to each other. The closure further may form or comprise a grip area by which the closure can be held and operated by a user of the device.

In one embodiment the cartridge comprises a cartridge body and separable therefrom a cartridge insert. The cartridge insert preferably comprises a container for containing the dental substance, and a dispensing end comprising the dispensing opening. The cartridge insert further may be received at least with the container in the cartridge body comprising the rear opening. Preferably the cartridge insert is received in a fill opening of the cartridge body. Thus the cartridge insert may be replaceable in the cartridge body by another cartridge insert, for example an empty cartridge insert may be replaceable by a new one. Accordingly the cartridge insert may form a disposable part of the device whereas other parts may be reusable. The closure may form part of the cartridge insert, for example may be fixed at the dispensing end of the cartridge insert. However the closure may further be separable from the cartridge insert, for example may be used with different cartridge inserts.

In one embodiment the cartridge insert comprises a foil bag for holding the dental substance and a hood received on one end of the foil bag. The other end of the foil bag is preferably closed, for example by a closure clip. A cartridge assembly may generally comprise the dental substance contained in a foil bag. The spindle may be arranged in the cartridge side by side with the foil bag as described above. Further two or more spindles may be arranged in the cartridge side by side with the foil bag. The spindle may further be arranged at least partially within the foil bag, for example may be pierced into the foil bag for dispensing the dental substance. Alternatively the foil bag may be generally cup shaped and receive the spindle within the cup. Such a cup shaped foil bag may be obtained in that a foil bag is not firmly filled with dental substance so that it can be deformed in such shape and only closed after shaping. In a particular embodiment the cartridge assembly comprises two foil bags each containing a component of a dental substance, and at least two spindles with the two foil bags arranged side by side between. Such embodiment may comprise a further spindle between the foil bags. The spindles may further be arranged for laterally supporting the foilbag(s). The individual spindles may be gear connected, for example adjacent an end of the spindles. The embodiments comprising the foils bag or bags may allow reuse of the spindle(s). This may help minimizing costs and waste in the use of the dental substances.

In one embodiment the dental substance is one of at least two components A and B of a dental impression material. The component or both components may consist of condensation cured or addition cured silicones which exhibit a consistency which can be kneaded by hand. Thus the components can be merged or mixed by a user, for example a dentist or dental assistant, by hand kneading. The components are further preferably adapted such that they can be relatively homogeneously mixed. The so prepared mixed dental impression material may be filled in a dental impression tray and placed in a patient's mouth for making a dental impression. The prepared dental impression material may be substantially non-sticky, for example may not stick to the device of the invention, meaning that the prepared dental impression material may be removable from a surface of the device generally without leaving residues behind.

The dental substance may therefore generally exhibit a consistency as it is described by ISO 4823 as kneadable or putty or type 0 consistency. ISO 4823 describes four different impression molding consistencies, namely a readily flowing consistency (type 3), a medium-flowing consistency (type 2), a poorly flowing consistency (type 1) and a kneadable consistency (type 0). For this purpose it is important that these type 0 materials do not stick to the fingers or gloves and/or leave residues behind. It is typical for these materials to have a high viscosity or consistency in the mixed paste which can be measured according to ISO 4823 and which shows a value of max. 35 mm. Such a high consistency can be achieved by using a high filler load or high viscous silicone polymers in the formulations of A and B.

The dental substance may further comprise isoparaffin or paraffin wax or microwax and/or liquid paraffin or liquid paraffin-coated fillers to them. This prevents the pastes sticking to the fingers. Materials of this nature are described, for example, in EP-A 0 219 660, EP-A 0 166 107, EP-A 0 158 141, EP-A 0 152 887 and U.S. Pat. No. 7,186,758 B2.

Condensation cured silicones generally consist of a silicone oil based on a polydimethylsiloxane containing hydroxyl end groups and mixed with fillers and a curing component containing a metal salt, e.g. of a monocarboxylic acid and a silicic acid ester as a crosslinking component. Examples of metal compounds are Dibutyltindilaurate or Titaniumalkoxides.

Preferred are addition curing silicones containing at least one organopolysiloxane having at least two unsaturated groups in the molecule, at least one organohydrogenpolysiloxane having at least or more than two SiH-groups in the molecule, a platinum catalyst, fillers and additives like those described to reduce stickiness but also pigments, plasticizers, antioxidants or surfactants.

The type 0 (ISO 4823) materials can also be based on condensation or addition curing polyethers and polyethersilicones. They are available in two components A and B which are mixed in a volume ratio of typically 10:1 to 1:10, preferably 1:1.

In a further embodiment the cartridge assembly has at least two cartridges. Each cartridge preferably comprises a dispensing opening. The cartridge assembly further may comprise for each of the cartridges a piston having a receptacle for establishing a screw connection with a spindle. Further the cartridge assembly may have a spindle arranged within each piston. Such a cartridge assembly may be used to store and dispense two different components which in combination may form a dental substance, for example a dental impression material.

In a further embodiment a dispensing device for dispensing a dental substance comprises the cartridge assembly of the invention. In particular the dispensing device may comprise a cartridge assembly having at least two cartridges with a piston for each of the cartridges. Each of the pistons may have a receptacle for establishing a screw connection with a spindle. Further each of the pistons may bear a spindle. Further each of the cartridges may comprise a component of the dental substance. The dispensing device may further comprise or be adapted to comprise a mixer for mixing the components to form the dental substance. Such dispensing device may have, preferably only have, a rotatable actuator for each piston for moving the piston for dispensing the dental substance. For example the device may not have a linearly movable plunger for moving the piston or pistons in the cartridge.

In one embodiment the cartridge assembly is removably placed or placeable in the dispensing device. Each rotatable actuator may comprise a coupling of the device which is adapted to engage with the coupling of the cartridge assembly. The coupling of the device may be displaceable axially with respect to a rotation axis of the rotatable actuator. However the coupling of the device is preferably displaceable for engaging the coupling of the device with the coupling of the cartridge assembly, rather than for moving the piston(s). The coupling of the device may by urged toward an engagement position by spring force and retractable against the spring force. For example the rotatable actuator may comprise a pin extending along a non-circular profile which is adapted to match with a socket in the coupling of the cartridge assembly having a corresponding counter-profile. An insertion of the cartridge in the device may cause the pin to retract or displace away from the engagement position, and upon rotation of the rotatable actuator the pin may and snap into the socket by displacing toward the engagement position as soon as the profiles of the pin and the socket are aligned with each other. In the engagement position the rotatable actuator may lock the cartridge assembly in the device.

In one embodiment the device is adapted to rotate the rotatable actuator in a dispensing direction and in a retracting direction opposite of the dispensing direction. Preferably the device is adapted to rotate the rotatable actuator in the retracting direction at a predetermined angle subsequent each rotation in the dispensing direction. Thus the piston(s) within the cartridge assembly may be somewhat retracted after dental substance has been dispensed and provide for releasing a pressure eventually built up within the cartridge assembly from pressing the dental substance(s) toward the dispensing opening(s). This may allow for preventing afterflow of the dental substance(s) after dispensation.

In operation the device may, via rotation of the spindle(s) in the cartridge assembly in a dispensing direction, move the piston for dispensing the material. The piston(s) may be retracted over a short distance for releasing pressure with the cartridge assembly. However a complete retraction of the piston or the spindle from the cartridge assembly may not be necessary. Thus the cartridge may be replaceable relative quickly in the device.

In a further embodiment the dispensing device comprises a drive shaft for driving the mixer. The drive shaft and the cartridge assembly may be coupled for moving the pistons of the cartridge. For example the drive shaft may have a coupling, for example a gear, for driving one or more gears of a cartridge assembly.

In a further aspect the invention relates to a method of assembling a cartridge assembly. The method comprises:

providing a non-assembled cartridge assembly according to the invention;

filling the cartridge with a dental substance;

placing the piston in the cartridge; and screwing the spindle into the piston such that at least a part of the spindle is screwed into the dental substance filled in the cartridge.

The method may allow for generally air free encapsulation of the dental substance with the cartridge assembly. This is because air may escape through the receptacle of the piston during the piston is placed in the cartridge.

In a further aspect the invention relates to use of a cartridge assembly, comprising a cartridge for containing a dental substance. The cartridge of the use comprises a dispensing opening for the dental substance. Further the cartridge assembly comprises a piston which has a receptacle for establishing a screw connection with a spindle for moving the piston. The movement of the piston enables urging the dental substance toward the dispensing opening. Further the use comprises a use of the cartridge assembly in a motor driven dispensing device, and optionally a use of the cartridge assembly manually. Alternatively the use comprises a use of the cartridge assembly manually, and optionally use of the cartridge assembly in a motor driven dispensing device.

DETAILED DESCRIPTION

Figure 1:
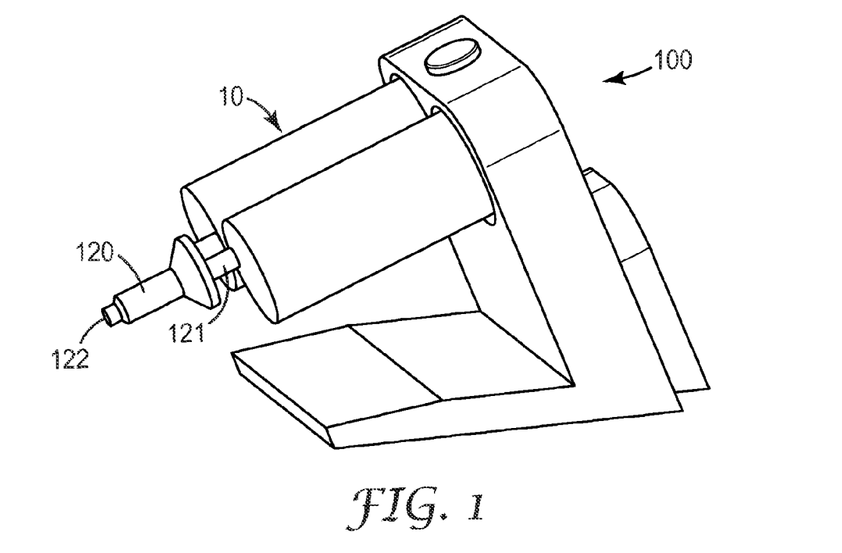
FIG. 1 is a perspective view of a device in combination with a cartridge assembly according to an embodiment of the invention.

FIG. 1 shows a device 100 for mixing and dispensing a dental substance. The device 100 shown is preferably used to mix and dispense a hardenable dental impression material. Such a dental impression material may be used to fill a dental tray which is then placed into a patient's mouth to take a dental impression.

The device 100 in the example shown is motorized and therefore allows for automatic mixing the dental substance from two individual substances or components and for automatic dispensation of the mixture. The device 100 is adapted to removably receive a cartridge assembly 10 and to extrude dental substances stored therein into a mixer 120. The mixer 120 is removably attached to the device 100 and/or the cartridge assembly 10 such that it can be replaced by a fresh mixer after use. The mixer 120 has a mixing chamber with inlets 121 for the individual dental substances and an opposite outlet 122 for the mixture. A mixing rotor (not shown) is arranged within the mixing chamber of the mixer 120 for mixing the dental substances in the mixing chamber as they flow through the mixer 120 from the inlets 121 toward the outlet 122. The device 100 is adapted to drive the mixing rotor by motor power. The device 100 thus implements a continuous dynamic mixing process in which dental substances can be continuously supplied into the mixer 120 so that the mixture from the substances is dispensed continuously from the mixer 120.

Figure 2:
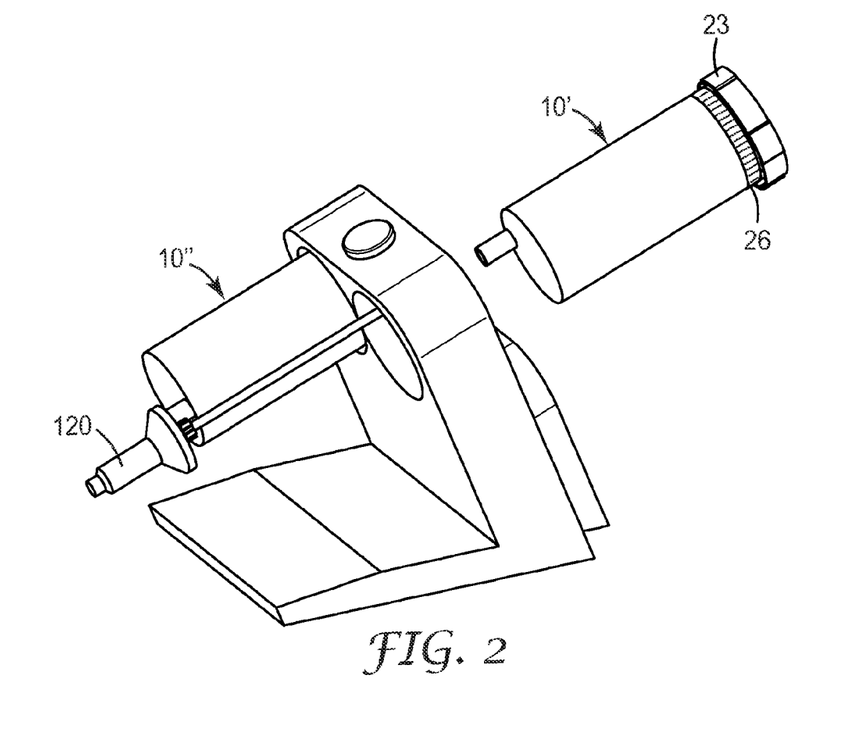
FIG. 2 is a further perspective view of the device in combination with the cartridge shown in FIG. 1.

FIG. 2 shows two separate cartridge assemblies 10' and 10". The cartridge assemblies 10' and 10" in combination generally correspond to the cartridge assembly 10 shown in FIG. 1. However in contrast to the cartridge assembly illustrated in FIG. 1 the cartridge assemblies 10' and 10" are separable from each other. Thus each of the cartridge assemblies may be used individually. Each cartridge assembly 10'/10" has as a first operation interface a handle 23 for manual operation of the cartridge assembly. Further each cartridge assembly 10'/10" has as a second operation interface a coupling 26 which in this case is formed by a gear structure. The handle 23 as well as the coupling 26 are mechanically connected to the spindle. Thus a rotation of either one of the handle 23 and the coupling 26 causes also the spindle to rotate. Therefore the cartridge assembly 10'/10" are adapted for use in a dispensing device and for manual use without a dispensing device. In a manual use of the cartridge assemblies 10'/10" dental substances may be dispensed from the individual cartridge assemblies 10'/10" and merged, for example kneaded by hand or mixed with a spatula on a mixing pad, whereas in the use with the dispensing device the dental substances may be mixed by the mixer 120 as described above. Therefore the cartridge assembly 10'/10" is preferably independent of the presence of a dispensing device, and thus may be relatively flexible in use.

Figure 3:
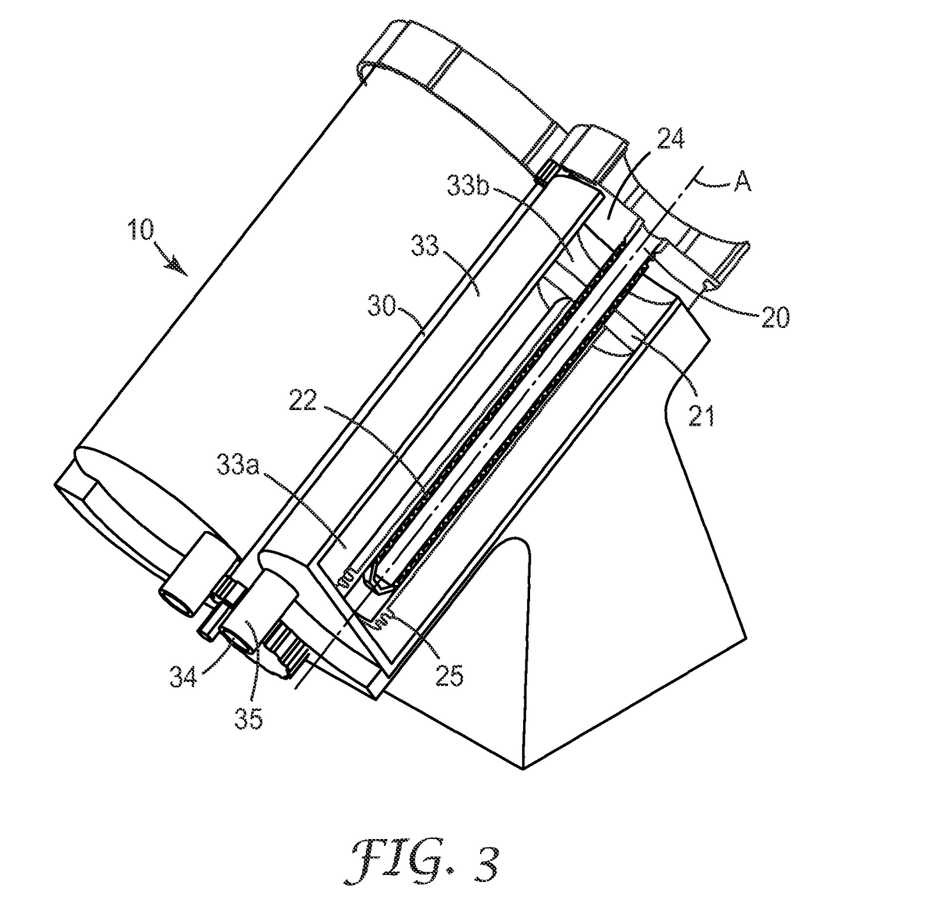
FIG. 3 is a perspective cross-sectional view illustrating details of a cartridge assembly according to an embodiment of the invention.

FIG. 3 shows in a cross-sectional view the cartridge assembly 10 in more detail. The cartridge assembly 10 has a cartridge 30 and a plunger assembly 20. The plunger assembly 20 has a piston 21 and a spindle 22. The spindle 22 is threaded and engages with a receptacle in the piston 21. In the example the receptacle comprises a through-hole through the piston and an inner thread which is adapted for forming a screw connection with an outer thread of the spindle 22.

Further the cartridge 30 forms a chamber 33 for containing the dental substance. The chamber 33 extends into a rear end of the cartridge 30 and opens in a dispensing opening 34 at a front end of the cartridge 30. Preferably the chamber 33 extends into the cartridge 30 at a generally uniform cross-section, in particular at a generally circular cross-section. The area of the cross-section of the chamber 30 is preferably greater than the area of the dispensing opening 34. In the example the dispensing opening 34 is formed in a nozzle 35 of the cartridge 30. However the dispensing opening may in another example be formed by a hole in a wall of the cartridge. The piston 21 is received within the chamber 33 and thus closes the rear end of the cartridge 30. The piston 21 is movable within the chamber 33 along a longitudinal axis A of the cartridge 30, in particular between the rear end and the front end of the cartridge 30. Thus the piston 21 is movable for advancing the dental substance toward the dispensing opening 34. The piston 21 divides the chamber 33 in a front partition 33a and a rear partition 33b. However the skilled person will recognize that in the extreme positions of the piston 21 relative to the chamber 33 there may be no or a very small front partition 33a or rear partition 33b. The volume of the front partition 33a is reduced as the piston 21 is moved further toward the dispensing opening so that the substance contained therein is displaced through the dispensing opening 34. The piston 21 and the cartridge 30 are preferably adapted (for example sized) to form a first press fit with each other in a situation in which the piston 21 is received within the chamber. Further the piston 21 and the spindle 22 are adapted (for example sized) to form a second press fit with one another. Preferably the first and second press fits are configured such that a torque required for rotating the piston 21 and the spindle 22 relative to each other is lower than a torque required for rotating the piston and the cartridge relative to each other. Therefore twisting the spindle 22 and the cartridge 30 relative to each other preferably causes the spindle 22 and the piston 21 to rotate relative other but not the piston 21 and the cartridge 30. The skilled person will recognize several ways of adjusting the first and second press fits to achieve this effect. For example in the first press fit an oversize of the piston 21 relative to the chamber 33 may be greater than in the second press fit between the spindle 22 and the receptacle of the piston 21. Further different material combinations may be used between the piston 21 and the cartridge 33 and on the other hand between the piston 21 and the spindle 22. For example a material combination providing less friction between the piston 21 and the spindle 22 than a material combination between the piston 21 and the cartridge 30 may be selected. The skilled person will be able to provide further solutions of providing differently tight first and second press fits, and in particular may combine features as mentioned above. The skilled person will further recognize that the cross-sections of the piston and the cartridge may be shaped non-circular, for example elliptical, to rotationally retain the piston and the cartridge relative to each other, but to permit axial displacement between these parts.

However the piston 21 preferably has a substantially circular cross-section and the chamber 33 may be formed by corresponding substantially circular walls of the cartridge 30. Thus the sealing quality between the piston 21 and the cartridge 30 may be maximized relative to any non-circular shape of the piston 21 and the cartridge walls. Further the piston 21 may comprise a lip seal (not shown), preferably a conically extending lip seal oriented with the cone widening (or greater cone diameter oriented) toward the dispensing opening 34. Such lip seal is preferably provided for sealing a gap between the piston 21 and the cartridge 30. Due to the orientation of the conical lip seal with the cone widening toward the dispensing opening 34 a pressure built up during pressurizing the dental substance toward the dispensing opening 34 preferably causes the lip seal to be urged toward the cartridge walls. Thus an increase of pressure in the dental substance preferably causes the seal effect between the piston 21 and the cartridge to improve. A further lip seal (not shown) may further be provided to provide a seal between the piston 21 and the spindle 22. Preferably such lip seal is also a conically extending lip seal, but oriented with the cone narrowing (or smaller cone diameter oriented) toward the dispensing opening 34. Due to the orientation of the conical lip seal a pressure built up during pressurizing the dental substance toward the dispensing opening 34 preferably causes the lip seal to be urged toward the spindle 22. Thus an increase of pressure in the dental substance preferably causes the seal effect between the piston 21 and the spindle 22 to improve. It has been found that although the lip seal may not perfectly seal on the thread of the spindle 22 the seal may be sufficient to prevent dental substance as used with the present invention to pass between the piston 21 and the spindle 22. Alternatively the lip seal may be made from a compressible material which optionally has an inner thread for conforming with the spindle thread. Such a seal may be compressed and may be urged tighter toward the spindle as the pressure in the dental substance increases. Thus the seal effect between the piston 21 and the spindle 22 may be maximized.

The cartridge assembly 10, and in particular the plunger assembly 20 comprises a support wheel 24 which supports and centers the spindle 22 within the chamber 33. The support wheel 24 may seal the rear end of the chamber 33. Further the chamber 33 may be predominantly sealed by a seal formed between the support wheel 24 and the cartridge 30. In contrast the piston 21 may just seal the partition 33a of the chamber 33 sufficiently to hinder the dental substance to flow from partition 33a toward partition 33b. Therefore the seal between the piston 21 and the spindle 22 may be sufficiently tight to block dental substance from passing the seal but loose enough to enable a movement between the piston 21 and the spindle 22. Nevertheless a hermetical seal may be provided between the cartridge 30 and the support wheel 24.

The spindle 22 is accommodated within the chamber 33 and carries the piston 21. Therefore a plunger for moving the piston 21 from outside the cartridge assembly 10 may not be necessary. Further additional space required for movement of such a plunger may be saved. This further helps minimizing the size of a dispensing device with which the cartridge assembly may be used because such device may not need any plungers for moving the piston(s) into the cartridge assembly. As illustrated the major part of the spindle or the entire spindle 22 is accommodated within the chamber 33. Thus preferably only a small or no part of the spindle 22 may extend out of the chamber 33. However in one example (not shown) the spindle may extend through the front end of the cartridge. Thus the spindle may be supported in the front end of the cartridge. Further the coupling may be arranged at an end of the spindle extending through the front end of the cartridge. This may allow driving the spindle from the front end so that the spindle pulls the piston toward the front end. Therefore the spindle may be minimized in diameter because a buckling load on the spindle may be minimized.

In a situation in which the cartridge 30 is filled with dental substance the spindle 22 therefore may extend into the front partition 33a and thus into the dental substance, as illustrated. The dental substance may be in direct contact with the spindle 22. In particular substantially no air may be entrapped between the spindle 22 and the dental substance. Thus the amount of air in the partition 33a may be minimized. Afterflow of the dental substance due to expanding air after releasing pressure from dispensing the dental substance may be prevented. The piston 21 optionally has a protection sleeve 25 into which the spindle 22 extends and which prevents direct contact between the spindle 22 and the dental substance. In this case substantially no air may be entrapped between the protection sleeve 25 and the dental substance. The protection sleeve 25 may be flexible such that it can be compressed as the piston 21 is moved for dispensing the dental substance. The protection sleeve 25 may be sealingly fixed at the piston 21 and closed at the opposite side. This may prevent the spindle 22 from getting contaminated from the dental substance and therefore may allow for the spindle 22 and the handle 23 to be reused, whereas the remainder of the cartridge assembly 10 may be disposable.

The diameter of the spindle 22 may be selected to control the capacity of the chamber 33, in particular the chamber partition 33a. Therefore also the amount of dental substance dispensed per rotation of the spindle 22 may be controlled. Alternatively the pitch of the spindle 22 may be selected to control the amount of dental substance dispensed per rotation of the spindle 22. This preferably allows for designing multiple cartridge assemblies generally identical, but just with different plunger assemblies. This may be advantageous for providing cartridge assemblies largely having parts of the same or similar design, but which provide for different ratios between the rotation of the plunger assembly and the amount of dental substance dispensed. For example a set of two cartridge assemblies for dispensing two dental substances to be mixed together at different mixing ratios (for example 2:1) may be provided by two largely similar cartridge assemblies but with different plunger assemblies only. This may further help minimizing manufacturing costs because different types of cartridge assemblies may be manufactured using the same standard parts and those standard parts may be pre-manufactured at relatively high volumes.

The cartridge assembly 10 may further comprise a ratchet (not shown) between the spindle 22 and the cartridge 30. The ratchet may provide for an audible click at certain rotational positions during a rotation of the screw. Therefore the ratchet may enable audible metering of the dispensed amount of dental substance, for example in case the cartridge assembly 10 is operated manually. Further the ratchet preferably permits free rotation of the spindle for dispensing the dental substance and limited rotation in the opposite direction for releasing the dental substance from pressure built up during dispensation.

Figure 4:
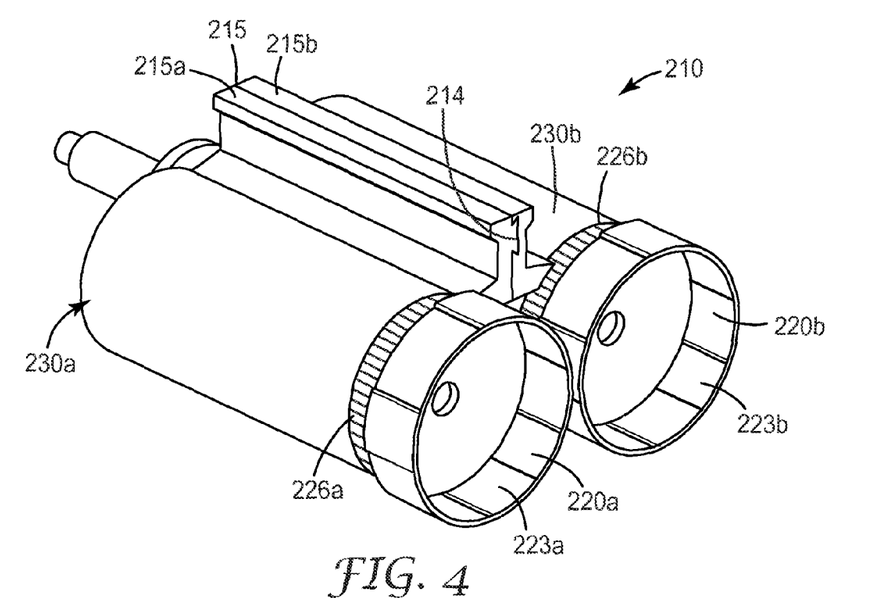
FIG. 4 is a perspective view of a cartridge assembly according to another embodiment of the invention.

FIG. 4 shows a cartridge assembly 210 which has two plunger assemblies 220a, 220b. Further the cartridge assembly 210 has two cartridge subassemblies 230a, 230b which are interconnected with each other to form a single unit. In the example the cartridge subassemblies 230a, 230b are connected by at least one dovetail 214. Further each of the cartridge subassemblies 230a, 230b has a partial grip portion 215a, 215b. In a situation where the cartridge subassemblies 230a, 230b are dovetailed with each other the partial grip portions 215a, 215b together form a common grip 215. Each of the cartridge subassemblies 230a, 230b has a handle 223a/223b allowing for manual dispensation of the dental substance from the cartridge assembly 210. Further each of the cartridge subassemblies 230a, 230b has a coupling 226a/226b allowing for the cartridge assembly 210 to be used as a single unit in a motor driven dispensing device.

Figure 5A:
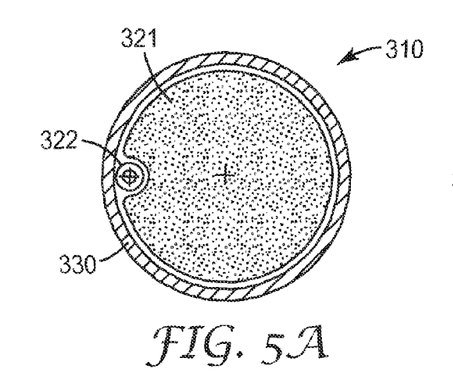
FIGS. 5A, 5B are cross-sectional views of a cartridge assembly according to a further embodiment of the invention.
Figure 5B:
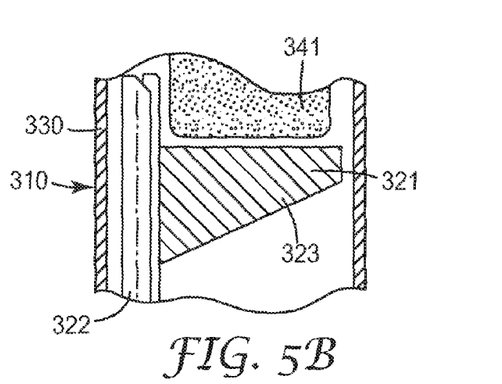

FIG. 5A shows a cartridge assembly 310. The cartridge assembly 310 has a cartridge 330 forming a generally cylindrical chamber and a spindle 322 which is arranged in an off-center relationship to the cylindrical chamber. As illustrated in FIG. 5B this may allow for accommodating the dental substance in a foil bag 341 which is placed within the cartridge 330. The spindle 322 in this embodiment is placed side by side with the foil bag 341. The cartridge assembly 310 further has a piston 321 which has a receptacle for establishing a screw connection with the spindle 322. Thus the spindle 322 may be rotated for moving the piston 321 forward and thus to urge the dental substance toward the dispensing opening (not visible) of the cartridge 330. The piston 321 may have a web 323 for limiting tilting of the piston 321 relative to the spindle 322, for example in case the piston is used for extruding dental substance from the cartridge assembly 310.

Figure 6:
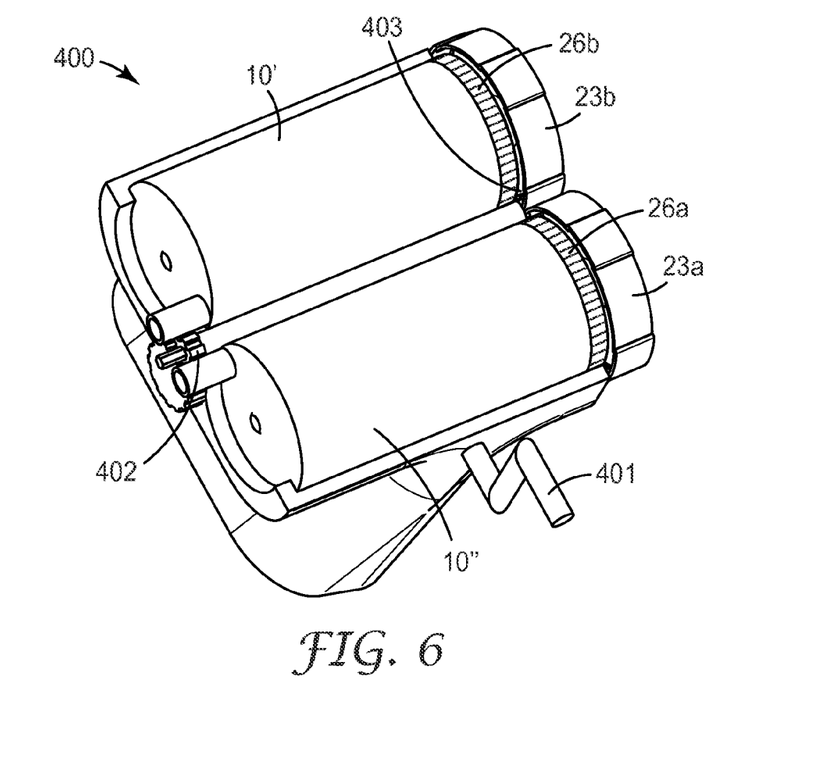
FIG. 6 is a perspective view of a further device in combination with a cartridge assembly according to an embodiment of the invention.

FIG. 6 shows two cartridge assemblies 10', 10" in combination with a manually operable dispensing device 400. In the example the device 400 has an actuator 401 which may be used to simultaneously dispense dental substances from the cartridge assemblies 10', 10". Optionally the device is adapted for receiving a dynamic mixer (not shown) for mixing the dental substances. The device 400 may therefore have a drive shaft 402 for driving such mixer. The drive shaft may be coupled to the actuator 401. Therefore the drive shaft 402 may rotate as the actuator is operated. The drive shaft 402 further has a gear 403 for driving the spindles (not visible) of the cartridges 10'/10" via driving the couplings 26a, 26b which are also in the form of gears, respectively.

The cartridge assemblies 10', 10" may alternatively be individually operated by use of the handles 23a, 23b. For example quantities of dental substance may be individually dispensed from the cartridge assemblies 10', 10" and merged manually after.

Figure 7:
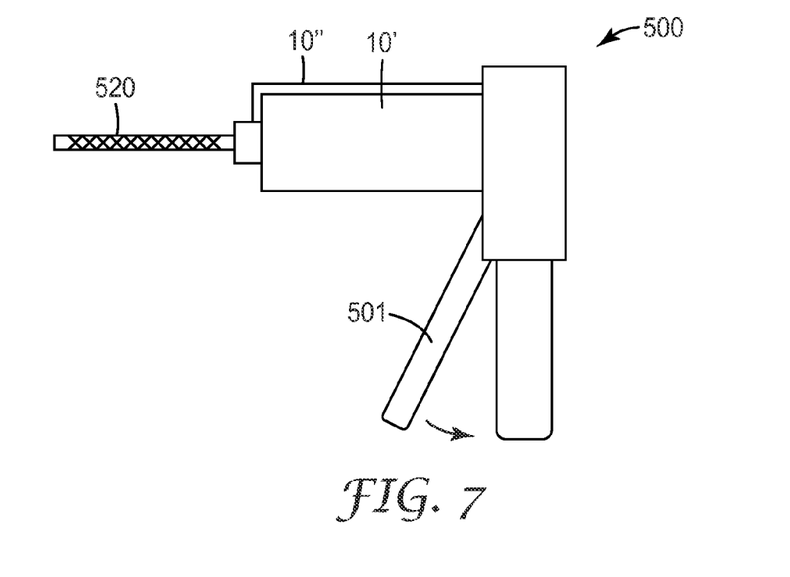
FIG. 7 is a side view of a still another device in combination with a cartridge assembly according to an embodiment of the invention.

FIG. 7 shows two cartridge assemblies 10', 10" in combination with a further manually operable dispensing device 500. The device 500 has an actuator 501 which may be used to dispense dental substances from the cartridge assemblies 10', 10". The device is adapted for receiving a static mixer 520 for mixing the dental substances.

In one example the cartridge assembly according to any of the embodiment described herein may be provided with a mount, for example a wall mount. Thus the cartridge assembly may be fixed at a place, for example in a dentist's practice, and operated with only one hand. Accordingly two cartridge assemblies for dispensing two components of a dental substance may be operated each by one hand simultaneously by one user. This may help minimizing time for preparation of the dental substance, for example and further may help saving space in a dental practice.

Figure 8A:
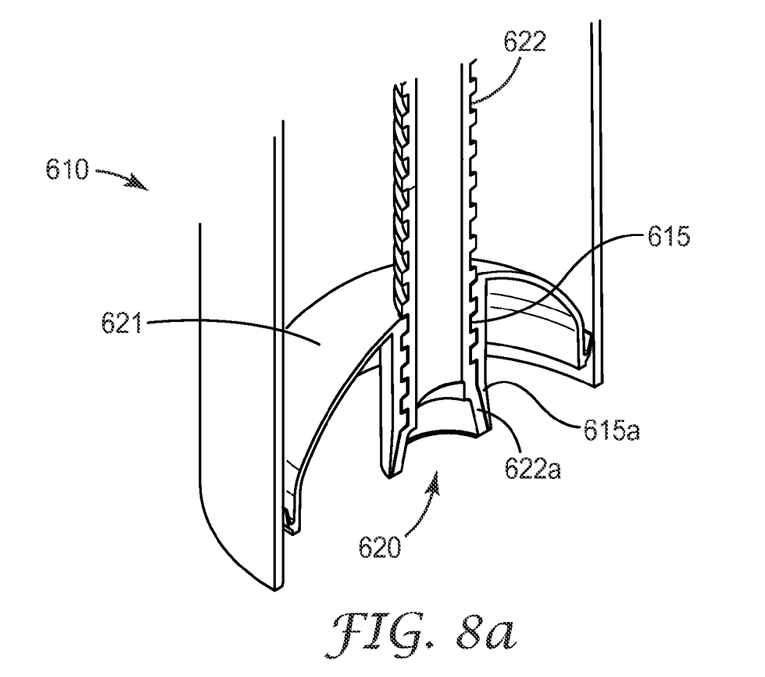
FIGS. 8a, 8b are cross-sectional views illustrating details of a further cartridge assembly according to an embodiment of the invention.

FIG. 8a illustrates in a cross-sectional view a cartridge assembly 610 with a plunger assembly 620 in a storage position. The storage position corresponds to a position of a new unused cartridge assembly. The piston 621 has an inner thread 615 extending through the piston 621 and engaging with a spindle 622. On a rear end of the piston which is facing the rear end of the spindle 622 the piston 621 has a seal 615a which extends circumferentially around the opening formed by the inner thread 615. In the storage position the seal 615a abuts at the spindle 622, in particular a sealing cone 622a at the spindle 622, so that the opening in the piston 621 formed by the inner thread 615 is sealed by the spindle 622. This allows a relatively good encapsulation of the dental substance in the unused cartridge assembly 610 during storage over a longer time (for example several months or years), and further allows a certain play between the inner thread of the piston 621 and the outer thread of the spindle 622. Latter further helps minimizing the force required to rotate the piston 621 and the spindle 622 relative to each other.

Figure 8B:
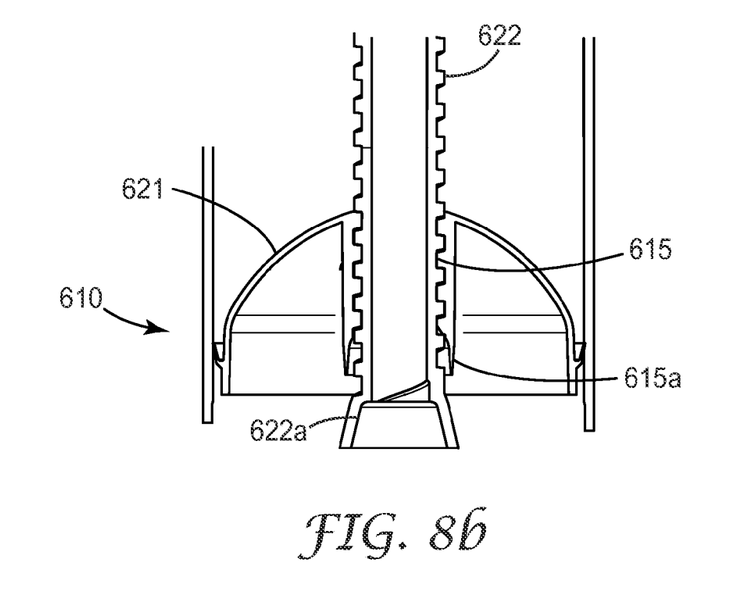

FIG. 8b shows the piston 621 positioned away from the storage position, for example in consequence of a dispensation of a portion of dental substance. The seal 615a is placed away from the sealing cone 622a of the spindle 622. Thus a space is present between the seal 615a and the sealing cone 622a which avoids any friction between the seal 615a and the sealing cone 622a during operation of the cartridge assembly 610.

The skilled person will recognize that certain features of embodiments described herein may be used for other embodiments described or not described herein. For example each of the embodiments may have a ratchet which allows for audible metering of a dental substance dispensed and for limiting any operation of the device which would cause the dental substance to be retracted.

Further each of the embodiments may have a closure allowing for cutting off a portion of a dental substance dispensed or multiple portions of multiple dental substances dispensed.

The invention claimed is:

1. A cartridge assembly being removably placeable in a dispensing device, comprising
    a cartridge for containing a dental substance, the cartridge comprising a dispensing opening for the dental substance and a generally cylindrical inner surface, wherein the dispensing opening has a smaller cross-sectional area than the generally cylindrical inner surface of the cartridge;
    a first operation interface allowing for manual operation of the cartridge assembly and a second operation interface allowing for machine operation of the cartridge assembly, wherein the second operation interface includes a coupling being formed by an outer gear structure, and wherein the first operation interface and the second operation interface are each located on an external surface of the cartridge;
    a spindle, and a piston having a receptacle for establishing a screw connection with the spindle for moving the piston to urge the dental substance toward the dispensing opening, wherein the coupling couples the spindle.

2. The cartridge assembly of claim 1, wherein the receptacle has a thread for engaging with a thread of the spindle, or wherein the receptacle is deformable and adapted for forming an engagement with a spindle thread by deformation through the spindle.

3. The cartridge assembly of claim 1, wherein the receptacle and the spindle are press fit for providing a seal between the receptacle and the spindle.

4. The cartridge assembly of claim 1, further comprising a support wheel for supporting the spindle in the cartridge.

5. The cartridge assembly of claim 1, comprising at least a component of a type 0 dental impression material.

6. The cartridge assembly of claim 1, having at least two cartridges, each cartridge comprising a dispensing opening, the cartridge assembly further comprising for each of the cartridges a piston having a receptacle for establishing a screw connection with a spindle.

7. A dispensing device for dispensing a dental substance, comprising the cartridge assembly of claim 6, wherein each of the cartridges comprises a component of the dental substance, the dispensing device further comprising a mixer for mixing the components to form the dental substance.

8. The dispensing device of claim 7, comprising drive shaft for driving the mixer, wherein the drive shaft and the cartridge assembly are coupled for moving the pistons of the cartridge.

9. The dispensing device of claim 7, wherein the cartridge assembly is removably placed in the dispensing device.

10. A dispensing device for dispensing a dental substance, comprising:
at least two cartridge assemblies of claim 1 being separable from each other and each removably placeable in the dispensing device.

11. The dispensing device of claim 10, further comprising a mixer coupled to the at least two cartridge assemblies for mixing the components of the dental substance.

12. The cartridge assembly of claim 1, wherein the receptacle comprises an inner cone and the spindle comprises an outer cone, and wherein the cartridge assembly is adapted such that the inner and outer cone in one position of the piston and the spindle relative to each other are in touch to seal the receptacle, whereas in another position of the piston and the spindle relative to each other the cones are spaced apart.

13. The cartridge assembly of claim 1, wherein the first operation interface and the second operation interface are both present during manual operation and machine operation of the cartridge assembly.

14. A dispensing device for dispensing a dental substance, the dispensing device comprising at least two cartridge assemblies of claim 1 being separable and independently operable from each other and each removably placeable in the dispensing device.

* * * * *